US010258733B2

United States Patent
Vasta

(10) Patent No.: US 10,258,733 B2
(45) Date of Patent: Apr. 16, 2019

(54) APPARATUS AND METHOD OF CONTROLLING AN EXTRACORPOREAL BLOOD TREATMENT

(71) Applicant: Gambro Lundia AB, Lund (SE)

(72) Inventor: Alessandro Vasta, Modena (IT)

(73) Assignee: Gambro Lundia AB, Lund (SE)

( * ) Notice: Subject to any disclaimer, the term of this patent is extended or adjusted under 35 U.S.C. 154(b) by 146 days.

(21) Appl. No.: 15/667,243

(22) Filed: Aug. 2, 2017

(65) Prior Publication Data
US 2017/0333616 A1 Nov. 23, 2017

Related U.S. Application Data

(63) Continuation of application No. 14/428,276, filed as application No. PCT/IB2013/056481 on Aug. 8, 2013, now Pat. No. 9,770,546.
(Continued)

(30) Foreign Application Priority Data

Sep. 28, 2012 (EP) ..................................... 12006803

(51) Int. Cl.
*A61M 1/36* (2006.01)
*A61M 1/34* (2006.01)
*A61M 1/16* (2006.01)

(52) U.S. Cl.
CPC ............ *A61M 1/3663* (2013.01); *A61M 1/16* (2013.01); *A61M 1/1613* (2014.02); *A61M 1/34* (2013.01);
(Continued)

(58) Field of Classification Search
CPC A61M 1/16; A61M 1/34; A61M 1/36; A61M 1/3624; A61M 1/3627;
(Continued)

(56) References Cited

U.S. PATENT DOCUMENTS 4,231,366 A 11/1980 Schael
4,570,484 A 2/1986 Sokalski
(Continued)

FOREIGN PATENT DOCUMENTS

CN 1678360 10/2005
CN 1747755 3/2006
(Continued)

OTHER PUBLICATIONS

International Search Report and Written Opinion dated Dec. 13, 2013, for related Intl. Appln. No. PCT/IB2013/056481.
(Continued)

*Primary Examiner* — Dirk R Bass
(74) *Attorney, Agent, or Firm* — K&L Gates LLP

(57) ABSTRACT

An apparatus is described for extracorporeal blood treatment, comprising a treatment unit, an extracorporeal blood circuit and a fluid evacuation line. The apparatus comprises a control unit connected to a pressure sensor and a blood pump, the blood pump generating a variable flow with a constant component and a variable component. The control unit receives, from the pressure sensor, a plurality of values and calculates the average pressure value, acquires an estimated value of volume variation in the expansion chamber connected to the variable flow component, calculates, as a function of the pressure values, an estimated value of pressure variation in the expansion chamber that is representative of an oscillating pressure component and determines a representative magnitude of a blood level in the expansion chamber as a function of the average pressure value, the estimated value of volume variation and the estimated pressure variation in the expansion chamber.

32 Claims, 7 Drawing Sheets

Related U.S. Application Data

(60) Provisional application No. 61/707,261, filed on Sep. 28, 2012.

(52) U.S. Cl.
CPC ............ *A61M 1/36* (2013.01); *A61M 1/3607* (2014.02); *A61M 1/3624* (2013.01); *A61M 1/3627* (2013.01); *A61M 2205/3306* (2013.01); *A61M 2205/3331* (2013.01); *A61M 2205/3334* (2013.01); *A61M 2205/3365* (2013.01); *A61M 2205/3375* (2013.01); *A61M 2205/3379* (2013.01); *A61M 2205/3389* (2013.01)

(58) Field of Classification Search
CPC ........ A61M 1/3663; A61M 2205/3331; A61M 2205/3389; A61M 1/1613; A61M 1/3607; A61M 2205/3306; A61M 2205/3334; A61M 2205/3365; A61M 2205/3375; A61M 2205/3379
USPC .......................................................... 210/137
See application file for complete search history.

(56) References Cited

U.S. PATENT DOCUMENTS

| | | |
|---|---|---|
| 7,013,727 B2 | 3/2006 | Delnevo |
| 7,435,235 B2 | 10/2008 | Sternby |
| 7,563,240 B2 | 7/2009 | Gross et al. |
| 7,985,196 B2 | 7/2011 | Kopperschmidt et al. |
| 8,091,407 B2 | 1/2012 | Schneider et al. |
| 8,430,834 B2 | 4/2013 | Kopperschmidt |
| 8,741,147 B2 | 6/2014 | Bene et al. |
| 2005/0119600 A1 | 6/2005 | Lucke et al. |

FOREIGN PATENT DOCUMENTS

| | | |
|---|---|---|
| CN | 1946441 | 4/2007 |
| CN | 101189509 | 5/2008 |
| CN | 101400387 | 4/2009 |
| CN | 101516418 | 8/2009 |
| EP | 0075606 | 4/1983 |
| EP | 2383003 | 11/2013 |
| WO | 0137899 | 5/2001 |

OTHER PUBLICATIONS

International Search Report and Written Opinion dated Dec. 2, 2013, for related Intl. Appln. No. PCT/IB2013/056495.

APPARATUS AND METHOD OF CONTROLLING AN EXTRACORPOREAL BLOOD TREATMENT

PRIORITY CLAIM

The present application claims priority to and the benefit as a continuation application of U.S. patent application Ser. No. 14/428,276, entitled "Apparatus and Method of Controlling an Extracorporeal Blood Treatment", filed Mar. 13, 2015, which is a National Stage Entry of International Application No. PCT/IB2013/056481, filed Aug. 8, 2013, which claims priority to European Patent Application No. 12006803.6, filed Sep. 28, 2012, and U.S. Provisional Application No. 61/707,261, filed Sep. 28, 2012, the entire contents of each of which are incorporated herein by reference and relied upon.

FIELD OF THE INVENTION

The present invention relates to an apparatus for extracorporeal blood treatment and to a method of controlling the apparatus.

BACKGROUND OF THE INVENTION

Known apparatus for extracorporeal treatment of blood include at least one treatment unit (for example a dialyser or a filter, or an ultrafilter or a plasma filter or a filter unit of any other nature) having a semipermeable membrane which separates the unit of treatment into two chambers. An extracorporeal blood circuit allows the circulation of blood taken from a patient internally of the first chamber. At the same time, and typically in a countercurrent direction to the blood, a treatment fluid is circulated through a special circuit in the second chamber of the treatment unit. This type of equipment for blood treatment, known as dialysis apparatus, can be used for the removal of solutes and excess fluid from the blood of patients suffering from renal failure.

The extracorporeal blood circuit also includes two expansion chambers, also called bubble-traps, respectively located on a blood removal line from the patient and on a return blood line to the patient.

The expansion chambers, during the treatment, contain a predetermined quantity of blood up to a predetermined depth and a predetermined quantity of gas (air) in the remaining part of the chamber.

Clearly, for a safe operation of the extracorporeal treatment, the level of blood must never fall below a critical minimum level that could lead to the introduction of air into the extracorporeal circulation lines and subsequent potential infusion of the air into the circulatory system of the patient, with serious consequences.

Since the risks of such an event exist, and the problems caused to the patient are extremely serious, if not critical, the known dialysis machines are equipped with safety systems that can detect such an event and, should it occur, can place the patient in safety.

In particular, a device is in general provided on the return line blood to the patient, just before the vascular access and downstream of the venous expansion chamber, which device is directly connected to the unit control of the machine and is for the detection of air bubbles in the blood.

In the event that air is detected in the venous line, the control unit activates a patient safety procedure for the isolation of the patient by at least closing clamps on the extracorporeal blood circuit and shutting down the blood pump.

In addition to this safety device, certain machines are also equipped with appropriate blood level sensors, optical or acoustic, in the venous expansion chamber (more rarely also in the arterial expansion chamber) able to signal the reaching of a minimum level that requires the intervention of specialized personnel to restore the correct quantity of blood in the chamber such as to avoid risks to the patient.

These systems, while fulfilling the tasks to which they are directed, incur additional costs and changes to the hardware of a machine on which they are or are to be installed.

Particularly because of the cost, these security systems are generally present only on the return line of the blood downstream of the dialyzer.

Furthermore, it is also worth mentioning that the bubble sensor device is generally able to reliably detect only bubbles of a predetermined size, while not possessing a sensitivity that would enable micro-bubbles of air dissolved in the blood to be detected.

There are recent studies (e.g. "Microemboli, developed during hemodialysis, pass the lung barrier and may cause ischemic lesions in organs such as the brain" by Ulf Forsberg, Per Jonsson, Christofer Stegmayr and Bernd Stegmayr) that have linked some typical disorders of chronic patients such as pulmonary hypertension and other ischemic problems with the quantity of air, in the form of micro-bubbles, generated by current dialysis machines and which are not disclosed by the current safety systems.

It should be noted in this regard that the generation of micro-bubbles occurs mainly because of the entry of air into the removal line, for example due to a low level of blood in the blood chamber (owing to various situations such as bad machine priming or infusion with air entry); in fact the bubbles that may get into the bloodstream and reach the dialyzer, which fragments them and makes them difficult to detect.

Also known from the U.S. Pat. No. 7,013,727 is a method for determining the blood level in a chamber of dialysis machines which exploits the ideal gas law in order to return to that level.

In particular, it exploits the change in blood volume in the chamber linked to the thrust generated on the blood by a peristaltic pump and, by means of two sensors (pressure and/or flow) the level in the chamber is detected.

This methodology, while enabling doing without a level sensor, typically requires additional hardware (a further sensor) in addition to that already present on the machine.

SUMMARY

An aim of the present invention is to disclose an apparatus for blood treatment able to detect a magnitude linked to the blood level in expansion chambers which can be an index of potential ingress of air into the extracorporeal blood circuit.

A further aim of the described embodiment is to provide an apparatus which may perform the said monitoring operation without any need for additional hardware with respect to the hardware already present on-board the machine.

A further auxiliary aim of the described embodiment is also to enable monitoring in the arterial expansion chamber and possibly also enabling monitoring in the venous expansion chamber to support the prevention systems already present in the machine.

A further aim of the described embodiment is to be applicable to machines already in use in clinical structures by means of an update to the operating software.

A further auxiliary aim of the described embodiment is such as to provide an apparatus which is able to perform this analysis reliably, reducing the false positives and increasing the detecting of the situations of risk.

A further auxiliary aim of the described embodiment is such as to provide an apparatus which in predetermined situations is able to intervene, automatically placing the patient in safety.

At least one of the above-indicated aims is substantially attained by a blood treatment apparatus according to one or more of any of the accompanying claims.

Aspects of the invention are illustrated in the following.

In a first independent aspect of the invention, an apparatus is provided for an apparatus for extracorporeal blood treatment comprising: at least a treatment unit (2) having at least a first chamber (3) and at least a second chamber (4) separated from one another by a semipermeable membrane (5); at least a blood removal line (6) connected to an inlet port of a first chamber and predisposed to remove blood from a patient; at least a blood return line (7) connected to an outlet port from the first chamber and predisposed to return treated blood to the patient; at least an expansion chamber (11, 12) placed at least in one of the blood removal line (6) and the blood return line (7), the expansion chamber being arranged in use to contain a predetermined quantity of gas in an upper portion and a predetermined quantity of blood at a predetermined level in a lower portion, the blood removal line (6), the blood return line (7), the first chamber (3) and the at least an expansion chamber (11, 12) being part of an extracorporeal blood circuit (8); at least a blood pump (9) operating at the extracorporeal blood circuit (8) such as to move the blood in the circuit; at least a pressure sensor (13, 14) associated to the expansion chamber (11, 12) and configured such as to enable determining pressure values internally of the expansion chamber (11, 12); at least a fluid evacuation line (10) connected to an outlet port of the second chamber; a control unit (21) connected to the at least a pressure sensor (13, 14), with the pump (9), and configured such as: to move the blood pump (9) such as to generate a variable blood flow (Q(t)) comprising a constant flow ($Q_b$) component of a desired blood flow value and a variable flow component ($Q_{var}(t)$) oscillating about the constant component ($Q_b$) and having a substantially nil average value, the variable blood flow ($Q_{var}(t)$) generating at least in the expansion chamber (11, 12) a pressure progression that is variable in time (P(t)) comprising a pressure component ($P_{var}(t)$) oscillating about a mean value ($P_{avg}$); to receive from the at least a sensor (13, 14) a plurality of pressure values ($P_j$) for a time period (T) comprising at least one, and in particular a plurality, of pressure oscillations about the means value ($P_{avg}$), the pressure values ($P_j$) being measured at successive time instants ($t_j$); to calculate, as a function of the pressure values ($P_j$), the average value ($P_{avg}$) of the pressure (P(t)); to acquire an estimated volume variation ($\Delta V$) in the expansion chamber (11; 12) linked to the variable flow component ($Q_{var}(t)$); to calculate, as a function of the pressure values ($\Delta P$), an estimated pressure variation value ($\Delta P$) in the expansion chamber (11; 12) that is representative of the oscillating pressure component ($P_{var}(t)$); to determine a magnitude that is representative of a blood level (L) in the expansion chamber (11, 12), as a function of the average value ($P_{avg}$) of the pressure (P(t)), of the estimated volume variation value ($\Delta V$) and the estimated pressure variation value ($\Delta P$) in the expansion chamber (11; 12).

In a 2nd aspect of the invention a method is provided for reduction of the risk of infusion of gas microbubbles in a patient in an apparatus for extracorporeal blood treatment and/or a detection method of the blood level in expansion chambers using an apparatus for extracorporeal blood treatment, the apparatus comprising: at least a treatment unit (2) having at least a first chamber (3) and at least a second chamber (4) separated from one another by a semipermeable membrane (5); at least a blood removal line (6) connected to an inlet port of the first chamber and predisposed to remove blood from a patient; at least a blood return line (7) connected to an outlet port from the first chamber and predisposed to return treated blood to the patient; at least an expansion chamber (11, 12) placed at least in one of the blood removal line (6) and the blood return line (7), the expansion chamber being arranged to use to contain a predetermined quantity of gas in an upper portion and a predetermined quantity of blood at a predetermined level in a lower portion, the blood removal line (6), the blood return line (7), the first chamber (3) and the at least an expansion chamber (11, 12) being part of an extracorporeal blood circuit (8); at least a blood pump (9) operating in the extracorporeal blood circuit (8) such as to move the blood in the circuit; at least a pressure sensor (13, 14) associated to the expansion chamber (11, 12) and configured such as to enable determining pressure values internally of the expansion chamber (11, 12); at least a fluid evacuation line (10) connected to an outlet port of the second chamber; the method includes carrying out a control procedure comprising: moving the blood pump (9) such as to generate a variable blood flow (Q(t)) comprising a constant flow component ($Q_b$) of a desired blood flow value and a variable flow component ($Q_{var}(t)$) oscillating about the constant component ($Q_b$) and having a substantially nil average value, the variable blood flow $Q_{var}(t)$ generating at least in the expansion chamber (11, 12) a pressure progression that is variable in time (P(t)) comprising a pressure component ($P_{var}(t)$) oscillating about a mean value ($P_{avg}$); to receive from the at least a sensor (13, 14) a plurality of pressure values ($P_j$) for a time period (T) comprising at least one, and in particular a plurality, of pressure oscillations about the means value ($P_{avg}$), the pressure values ($P_j$) being measured at successive time instants ($t_j$); to calculate, as a function of the pressure values ($P_j$), the average value ($P_{avg}$) of the pressure (P(t)); to acquire an estimated volume variation ($\Delta V$) in the expansion chamber (11; 12) linked to the variable flow component ($Q_{var}(t)$); to calculate, as a function of the pressure values ($\Delta P$) in the expansion chamber (11, 12) that is representative of the oscillating pressure component ($P_{var}(t)$); to determine a magnitude that is representative of a blood level (L) in the expansion chamber (11, 12), as a function of the average value ($P_{avg}$) of the pressure (P(t)), of the estimated volume variation value ($\Delta V$) and the estimated pressure chamber (11; 12).

In a 3rd aspect according to the preceding aspects, the control procedure (or the control unit 21) is programmed to determine the representative magnitude of the blood level in the expansion chamber (11; 12), for example an air volume ($V_{air}$)) in the expansion chamber (11; 12), for example a volume of air ($V_{air}$)) in the expansion chamber (11, 12), by exploiting the ideal gas law.

In a 4th aspect according to the preceding aspect, the ideal gas law is applied to a modelled representation of the apparatus substantially constituted by a superposing of:

an open system in which the expansion chamber (11, 12) is considered to be in a stationary state and interested only by the constant flow component ($Q_b$) and the internal pressure in the expansion chamber is correspondingly a constant pressure equal to the mean value ($P_{avg}$); and a partially closed system in which only an access to the expansion chamber (11, 12), selected from between an inlet (11a, 12a) for the blood and an outlet (11b, 12b) for the blood, is open and subject to a volume variation ($\Delta V$) representative of the variable flow component ($Q_{var}(t)$) oscillating about the constant component ($Q_b$) and a pressure value ($\Delta P$) representing the oscillating pressure component ($P_{var}(t)$).

In a 5th aspect according to the preceding aspects, the control procedure (or control unit 21) is programmed such as to determine the magnitude representing a blood level (L) in the expansion chamber (11, 12) using the following mathematical relation:

$$V_{air} = \Delta V \frac{(Pavg + \Delta P)}{(\Delta P)}$$

in which: '$V_{air}$' is the volume of air inside the expansion chamber (11; 12); '$\Delta V$' is the volume variation linked to the variable flow component (Qvar(t)); '$P_{avg}$' is the average pressure value (P(t)); '$\Delta P$' is the pressure variation in the expansion chamber (11, 12) representing the oscillating pressure component ($P_{var}(t)$).

In a 6th aspect according to the preceding aspects, the average pressure value ($P_{avg}$) is calculated as a function of a plurality of measured pressure values ($P_j$) relating to a time period (T) comprising a plurality of blood flow oscillations about the constant component ($Q_b$) and consequently a plurality of oscillations of the pressure about the average value ($P_{avg}$), in particular the time period (T) comprising at least three oscillations and still more in detail at least eight oscillations.

In a 7th aspect according to the preceding aspect, the time period (T) is a function of the constant component of blood flow ($Q_b$)

In an 8th aspect according to the preceding aspects, the step of acquiring an estimated value of volume variation ($\Delta V$) in the expansion chamber (11, 12) comprises a sub-step of reading from a memory of an estimated pre-set value of volume variation ($\Delta V$), for example an estimated value entered by an operator or an estimated value selected by the control unit (21) from among a plurality of possible pre-set estimated values, the selection being in particular operated according to at least one or more of the following parameters: a type of extracorporeal circuit installed on the apparatus; a type of extracorporeal blood treatment; a type of blood pump; the desired blood flow value ($Q_b$); a pressure upstream or downstream of the blood pump (9); a type of pump tract (6a); the average pressure ($P_{avg}$) in the expansion chamber (11; 12); an index of ageing of the pump tract (6a); the number of revolutions accumulated by the blood pump (9).

In a 9th aspect according to the preceding aspects from 1 to 7, the step of acquiring an estimated value of volume variation ($\Delta V$) in the expansion chamber (11; 12) comprises a sub-step of calculating the estimated value as a function of at least the pressure values ($P_j$) measured.

In a 10th aspect according to the preceding aspects from 1 to 7 or 9, the step of acquiring an estimated value of volume variation ($\Delta V$) in the expansion chamber (11; 12) comprises a sub-step of calculating the estimated value as a function of at least the value of the constant component of blood flow ($Q_b$).

In an 11th aspect according to the preceding aspects from 1 to 7, 9 or 10, the step of acquiring an estimated value of volume variation ($\Delta V$) in the expansion chamber (11; 12) comprises a sub-step of calculating the estimated value as a function of at least an indicator of an ageing of a pump tract (6a), the indicator for example being the number of revolutions of the pump (9) accumulated at the moment of the estimation of volume variation ($\Delta V$) in the expansion chamber (11; 12) or the number of pulses of an encoder which detects passage of rollers of a blood pump (9) of a peristaltic type.

In a 12th aspect according to preceding aspects from 1 to 7 or from 9 to 11, the step of acquiring an estimated value of volume variation ($\Delta V$) in the expansion chamber (11; 12) comprises a sub-step of calculating the estimated as a function at least of a preceding estimated value of a variation in air volume ($V_{j-1}$) in the expansion chamber (11; 12).

In a 13th aspect according to the preceding aspects from 1 to 7 or from 9 to 12, the step of acquiring an estimated value of volume variation ($\Delta V$) in the expansion chamber (11; 12) comprises a sub-step of calculating the estimated value using the following mathematical relation:

$$\Delta V_n = k_0 + k_1 \cdot \overline{P_n} + k_2 \cdot n_{imp_n} + k_3 \cdot \overline{Q_{b_n}} + k_4 \cdot V_{n-1}$$

in which: n is the generic index indicating the n-th measurement output of the air volume ($V_{air}$); $\Delta V_n$ is the estimated variation of volume $\Delta V$ at the nth step of measurement of the air volume ($V_{air}$); $k_0$, $k_1$, $k_2$, $k_3$, $k_4$ are experimentally-determined constants; $\overline{P_n}$ is the average of the pressure values measured at the end of the nth measuring step of the air volume ($V_{air}$); $n\_imp_n$ is the accumulated number—or a value proportional to the accumulated number—of revolutions of the blood pump (9); is the average value of the blood flow at the end of the n-th measuring step of the air volume ($V_{air}$); $V_{n-1}$ is the estimated measurement of the air volume obtained from the preceding calculation.

In a 14th aspect according to the preceding aspect, the mathematical relation is adopted in the event that the average value of the blood flow ($Q_b$) is less than 400 ml/min and in particular greater than 100 ml/min.

In a 15th aspect according to preceding aspects from 1 to 7 or from 9 to 12, the step of acquiring an estimated value of volume variation ($\Delta V$) in the expansion chamber (11, 12) comprises a sub-step of calculating the estimated value using the following mathematical relation:

$$\Delta V_n = k_0 + k_1 \cdot \overline{P_n} + k_2 \cdot n_{imp_n} + k_3 \cdot \overline{Q_{b_n}} + k_4 \cdot V_{n-1} + k_5 \cdot \overline{P_n^2}$$

in which: n is the generic index indicating the n-th measurement output of the air volume ($V_{air}$); $\Delta V_n$ is the estimated variation of volume $\Delta V$ at the n-th step of measurement of the air volume ($V_{air}$); $k_0$, $k_1$, $k_2$, $k_3$, $k_4$, $k_5$ are experimentally-determined constants; $\overline{P_n}$ is the average of the pressure values measured at the end of the nth measuring step of the air volume ($V_{air}$); $n\_imp_n$ is the accumulated number—or a value proportional to the accumulated number—of revolutions of the blood pump (9); is the average value of the blood flow at the end of the nth measuring step of the air volume ($V_{air}$); $V_{n-1}$ is the estimated measurement of air volume obtained with the preceding calculation.

In a 16th aspect according to the preceding aspect, the mathematical relation is adopted in a case where the average value of the blood flow ($Q_b$) is greater than 300 ml/min and in particular less than 650 ml/min.

In a 17th aspect according to the preceding aspects, the step of calculating an estimated value of pressure variation (ΔP) is carried out using a mathematical relation which is a function of a statistical indicator (VarStat) representative of the oscillating pressure component (ΔP): $\Delta P = f^{\{VarStat\}}$ In an 18th aspect according to the preceding aspect, the statistical indicator (VarStat) is a dispersion index summarily describing a quantitative statistical distribution of the measured pressure values ($P_j$), in particular in which the statistical indicator is a measurement indicating a distance of the pressure values ($P_j$) from a central value, for example, identified with the average value ($P_{avg}$) of the pressure.

In a 19th aspect according to the preceding aspects 17 or 18, the statistical indicator (VarStat) is the standard deviation (σ(P)) or the integral average (MI), in particular the demodulated integral average.

In a 20th aspect according to preceding aspects from 17 to 19, the statistical index (VarStat) of the pressure values measured ($P_j$) is calculated on a plurality N of measured pressure values ($P_j$), in particular N being greater than 6 and still more in particular N being at least 10.

In a 21st aspect according to the preceding aspects, the step of calculating an estimated value of pressure variation (ΔP) is carried out by means of a mathematical relation that is a function of a statistical indicator (VarStat) which represents the oscillating pressure component (ΔP) and a constant obtained experimentally ($K_{form}$): $\Delta P = K_{form} \cdot VarStat$ In a 22nd aspect according to the preceding aspect, the statistical indicator (VarStat) representing the oscillating pressure component (ΔP) is defined as:

$$\sigma(P) = \sqrt{\sum_{t=1}^{N} \frac{(P_t - \overline{P})^2}{(N-1)}}$$

in which: N is the number of pressure measurements carried out in the reference time interval ($T_n$) comprising a plurality of pressure oscillations ($P_j$); $P_i$ is the generic i-th pressure measurement; $\overline{P}$ is the average pressure calculated in the reference time interval ($T_n$).

In a 23rd aspect according to the preceding aspects from 1 to 15, the statistical indicator (VarStat) representing the oscillating pressure component (ΔP) is defined as:

$$\sigma(P) = \frac{1}{N} \cdot \sum_{t=1}^{N} (P_t - \overline{P}) \cdot demod(i)$$

in which: N is the number of pressure measurements carried out in the reference time interval ($T_n$) comprising a plurality of pressure oscillations ($P_j$); $P_i$ is the generic i-th pressure measurement; $\overline{P}$ is the average pressure calculated in the reference time interval ($T_n$); demod(i) is a square wave of single amplitude synchronised with the blood pump (9) and in phase with the peristaltic pulse.

In a 24th aspect according to the preceding aspects, the expansion chamber is an arterial expansion chamber (11) located on the blood removal line (6).

In a 25th aspect according to the preceding aspect, the blood pump (9) is located downstream of the arterial expansion chamber (11) along a blood transit direction.

In a 26th aspect according to the preceding aspects, the expansion chamber is a venous expansion chamber (12) located on the blood return line (7).

In a 27th aspect according to the preceding aspects, the control procedure (or control unit 21) carries out the steps of the first or second aspect in relation to an arterial expansion chamber (11) located on the blood return line (6).

In a 28th aspect according to the preceding aspect, the control procedure (or control unit 21) carries out the steps of the first or second aspect in relation to a venous expansion chamber (12) located on the blood return line (7).

In a 29th aspect according to the preceding aspect, the control procedure (or control unit 21) carries out the steps of the first or second aspects in relation both to an arterial expansion chamber (11) located on the blood removal line (6) and to a venous expansion chamber (12) located on the blood return line (7).

In a 30th aspect according to the preceding aspects, the blood pump (9) is a peristaltic pump.

In a 31st aspect according to the preceding aspects, the pressure sensor (13, 14) is located in the expansion chamber (11, 12), in particular at the portion in use arranged to contain the gas.

In a 32nd aspect according to the preceding aspects, the expansion chamber (11, 12) exhibits an inlet (11a, 12a) for the blood in fluid connection with the extracorporeal circuit (8) such as to receive, in use, blood in inlet to the chamber and an outlet (11b, 12b) for the blood in fluid connection with the extracorporeal circuit (8) such as to cause to flow, in use, blood in outlet from the chamber, the inlet (11a, 12a) and the outlet (11b, 12b) being positioned at a base portion of the expansion chamber (11, 12) arranged, in use, to be facing downwards and in particular always occupied by the blood.

In a 33rd aspect according to the preceding aspects, the expansion chamber (11, 12) exhibits a ventilation opening (15, 16) configured such as to allow, in use, a passage of gas from to towards the expansion chamber (11, 12), the apparatus further comprising at least an actuator (17, 18) operating on the ventilation opening (15, 16) such as to selectively inhibit or enable the passage of gas, the ventilation opening (15, 16) being in particular positioned at an upper portion of the expansion chamber (11, 12) arranged, in use, to be facing upwards, and still more in particular arranged to be always occupied by the gas.

In a 34th aspect according to the preceding aspect, the control procedure (or control unit 21) in the event of a verification of a blood level in the expansion chamber (11, 12) below a predetermined threshold ($L_{min}$), commands the actuator (17, 18) such as to enable passage of gas through the ventilation opening (15, 16).

In a 35th aspect according to the preceding aspect, the control procedure (or control unit 21) in the event of a verification of a blood level in the expansion chamber (11, 12) below a predetermined threshold ($L_{min}$), commands the actuator (17, 18) such as to enable passage of gas in exit from the ventilation opening (15, 16).

In a 36th aspect according to the preceding aspects, the control procedure (or control unit 21) in the event of a verification of a blood level in the expansion chamber (11, 12) below a predetermined threshold ($L_{min}$), commands actuator active at least on the extracorporeal blood circuit (8) such as to place the patient in a condition of safety.

In a 37th aspect according to the preceding aspects, the control procedure (or control unit 21) in the event of a verification of a blood level in the expansion chamber (11, 12) below a predetermined threshold ($L_{min}$), commands at least the blood pump (9) such as to reduce or zero the blood flow in the extracorporeal blood circuit (8) and substantially annuls the passage of fluid through the semipermeable membrane (5) of the treatment unit (2).

In a 38th aspect according to the preceding aspects, the control procedure (or control unit 21) activates at least the blood pump (9) before the start of a treatment for creating in the expansion chamber (11, 12) the established level of blood in the lower portion and confines a complementary quantity of gas in the upper portion.

In a 39th aspect according to any one preceding aspect, the apparatus comprises at least a device (19) for detection of air bubbles in the blood located on the extracorporeal blood circuit (8), the device (19) being in particular located on the blood return line (7) and still more particularly downstream of a venous expansion chamber (12) along the flow direction of the blood in the extracorporeal circuit.

In a 40th aspect according to any one preceding aspect, the apparatus further comprises at least an intercept organ of the blood flow (20, 22) active on the extracorporeal circuit (8) downstream of a venous expansion chamber (12) along the flow direction of the blood in the extracorporeal circuit.

In a 41st aspect according to the preceding aspect, the apparatus further comprises two intercept organs of the blood flow (20, 22) active on the extracorporeal circuit (8), one (22) downstream of a venous expansion chamber (12) along the blood flow direction in the extracorporeal blood circuit, the other (20) upstream of an arterial expansion chamber (11), in particular each of the intercept organs of the blood flow (20, 22) comprising a respective clamp respectively active on the blood return line (7) and on the blood removal line (6), the control unit (21) being active on the intercept organs (20, 22) such as to command the intercepting or not of the flow.

In a 42nd aspect according to the preceding aspect, the control procedure (or control unit 21) compares the calculated blood level (L) with at least one of a maximum admissible threshold ($L_{max}$) and a minimum admissible threshold ($L_{min}$) in order to determine whether the blood level is within a correct functioning interval ($L \leq L_{max}$; $L \geq L_{min}$) and to signal a malfunction in the event that the blood level is beyond the correct functioning level.

DESCRIPTION OF THE DRAWINGS

Some drawings are given below by way of non-limiting example, related to aspects of the invention.

In particular.

DETAILED DESCRIPTION

With reference to the accompanying drawings, 1 denotes an apparatus for the extracorporeal treatment of blood.

The apparatus 1 comprises an extracorporeal circuit arranged to extract blood from the cardiovascular system of a subject, for example a patient P, and return the treated blood to the patient.

Below some possible examples are described relating to the general structure of the apparatus 1: in particular some configurations of the extracorporeal blood circuit are described, as well as the infusion lines, if present, in which a replacement fluid circulates, any dialysis line in which a dialysis fluid circulates, and the waste fluid discharge line.

Figure 1:
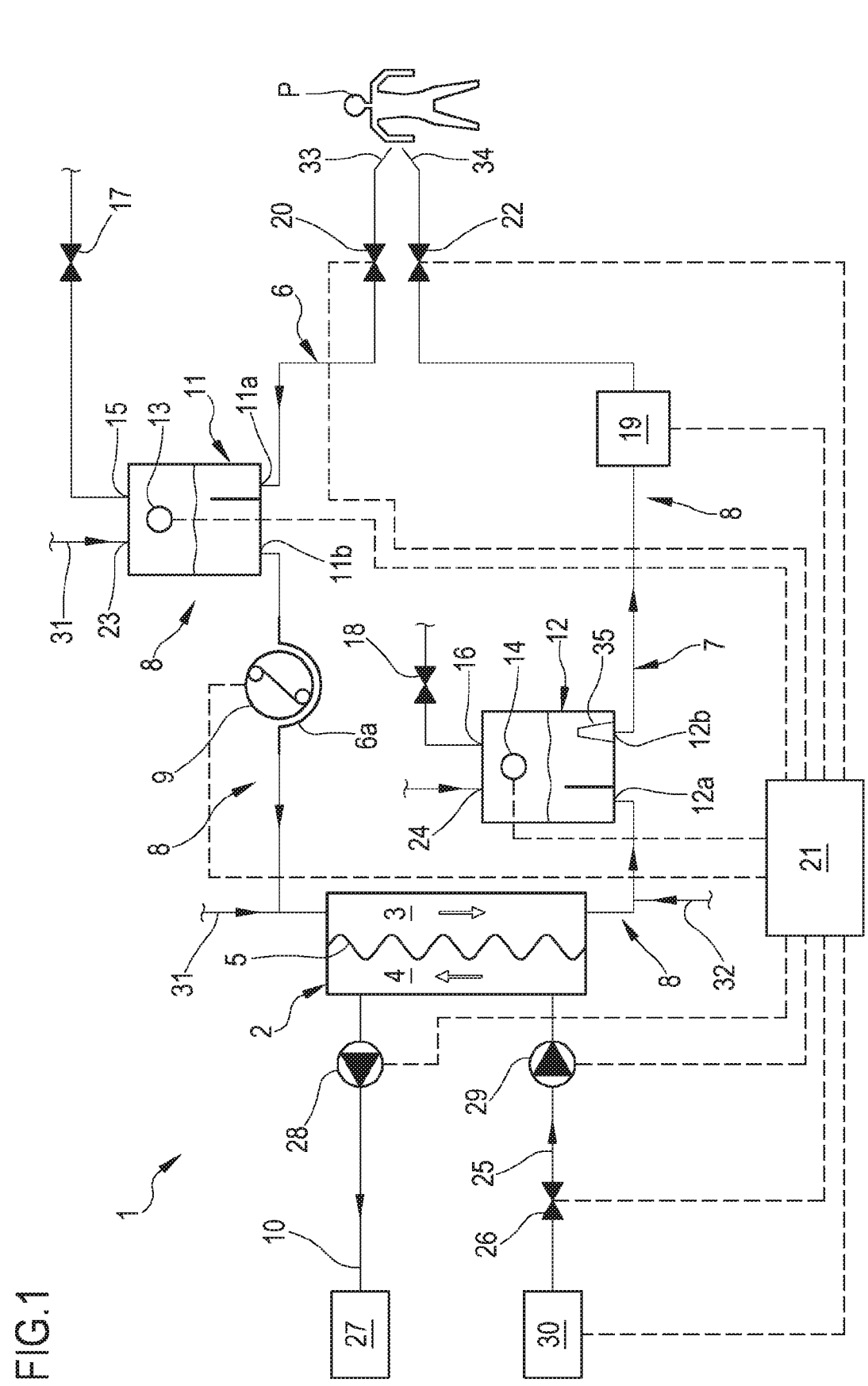
FIG. 1 schematically illustrates a blood treatment apparatus, according to the invention.

With reference to FIG. 1, the apparatus for the extracorporeal treatment of blood comprises at least a treatment unit 2, for example a hemofilter, a hemodiafilter, a plasmafilter, a dialysis filter, a membrane oxygenator or other units also suitable for processing the blood taken from the patient, having at least a first chamber and at least a second chamber 3 and 4 separated from one another by a semipermeable membrane 5. A blood removal line 6 is connected to an inlet port 11a of the first chamber 3 and is predisposed, in operative conditions of connection to a patient, to remove blood from a vascular access inserted, for example in a fistula on the patient. A blood return line 7 connected to an outlet port 11b of the first chamber is predisposed to receive the treated blood from the treatment unit and to return the treated blood to a vascular access also connected to the fistula of the patient. Note that the configuration of the vascular access may be of any nature: for example, a catheter, a port implanted in the patient, a cannula, a needle, and so on.

Figure 2:
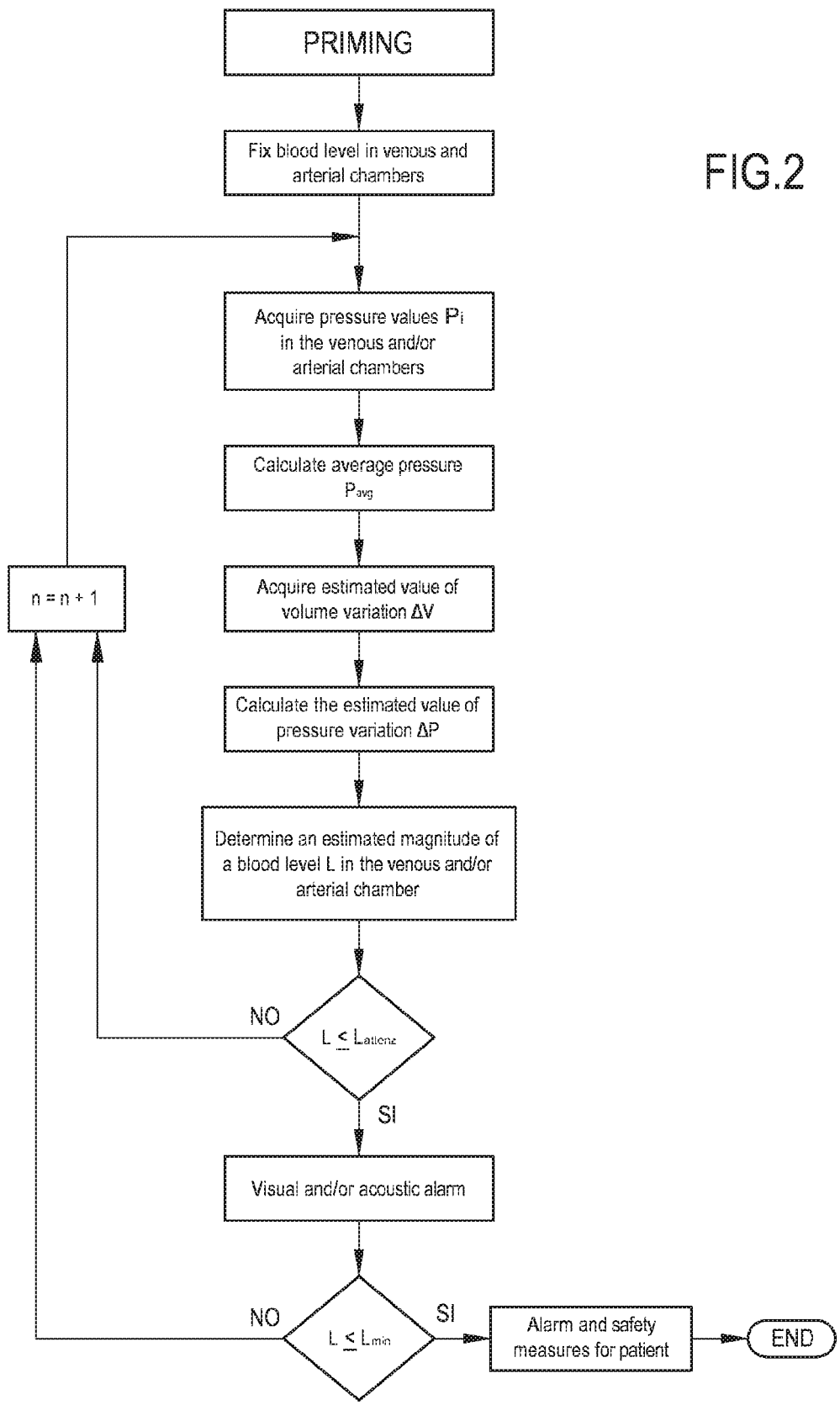
FIG. 2 is a flow diagram illustrating a control procedure according to an aspect of the invention, performable by the control unit of an apparatus for example of the type shown in FIG. 1.

As can be seen in FIG. 1, the apparatus 1 comprises at least a first actuator, in the present example a blood pump 9, which operates at a blood removal line such as to facilitate the movement of the blood removed from the patient from the first end 33 of the removal line 6 connected to the patient P to the first chamber 3; the blood pump 9 is, for example, an active peristaltic pump, as shown in FIGS. 1 and 2, on a respective tube section 6a and able, when moved in a clockwise direction, to move a flow of blood along the removal line towards the first chamber 3 (see the arrows indicating the flow along this line).

It should be noted that for the purposes of the present description and the appended claims, the terms "upstream" and "downstream" may be used with reference to the relative positions assumed by components belonging to or operating on the extracorporeal circuit. These terms are to be understood with reference to a blood flow direction from the first end 33 of the removal line 6 connected to the patient P towards the first chamber 3 and then towards the second end 34 of the return line 7 connected to the vascular access of the patient P.

In the example of FIG. 1, the extracorporeal circuit comprises at least an expansion chamber 11 acting on the arterial blood removal line 6 from the patient P and arranged upstream with respect to the first chamber 3 and upstream with respect to the blood pump 9.

This chamber 11 receives the blood directly from the patient and accumulates a set amount that will remain substantially constant throughout the treatment.

At least a pressure sensor 13 is predisposed to detect at least a parameter relating to the pressure of the fluid present in the arterial expansion chamber 11.

In general, the sensor 13 is configured such as to emit a signal corresponding to a measured value of the parameter, then sending it to a control unit 21 each time a measurement is carried out in successive moments of time Note that it is possible to perform the detection of the pressure parameter also in close proximity of the arterial expansion chamber 11, for example by means of a transducer located either in the section of pipe between the expansion chamber 11 and the arterial blood pump 9, or in the stretch of piping between the expansion chamber 11 and the arterial vascular access to the patient P.

In any case, in a possible proper positioning of the pressure sensor 13, the pressure sensor 13 is directly active in the arterial expansion chamber 11 at an upper portion thereof where normally (in use) a gas (air) is housed.

It should be noted in fact that the arterial expansion chamber 11 is generally arranged in use and during treatment to accommodate an amount of gas into an upper portion and an amount of blood at a set level in a lower portion thereof.

The expansion chamber 11 has an inlet 11a for the blood that is in fluid connection with a first part of removal line 6 connected to the vascular access of the patient P.

The chamber 11 receives blood entering the chamber through the inlet 11a. In general, the inlet 11a may be positioned at a base portion of the expansion chamber arranged, in use, to be directed downwards and in particular always occupied by blood.

In an embodiment the inlet may be connected to a channel internal of the arterial expansion chamber 11 which has an outlet in the chamber itself at a predetermined height with respect to the base.

The arterial expansion chamber also includes an outlet 11b for the blood in fluid connection with the extracorporeal circuit 8, which causes, in use, the flow of blood in outlet from the chamber. The outlet 11b is also positioned at a base portion of the expansion chamber 11 arranged, in use, to be directed downwards and in particular always occupied by blood.

The portion of the removal line 6 which connects the outlet 11b of the arterial expansion chamber 11 to the first chamber 3 of the treatment unit 2 comprises a pump section 6a which is engaged by the peristaltic pump 9 such as, through squeezing the same tract of tube, to move the blood in the extracorporeal circuit.

A particular type of peristaltic pump 9 may be provided with two crushing bodies (rollers) that act on the pump portion 6a twice for each rotation of the blood pump 9.

The expansion chamber 11 has also a ventilation opening 15 configured to allow, in use, a passage of gas into or from the expansion chamber 11 itself, for example to or from the external environment.

The apparatus further comprises at least an actuator 17 operating on the ventilation opening 15 (for example a funnel connected thereto) for selectively inhibiting or enabling the passage of gas. The ventilation opening 15 is in particular positioned at an upper portion of the expansion chamber 11 intended, in use, to be facing upward, and even more in particular intended to be always occupied by the gas.

The actuator 17 may be an air pump or even a simple clamp (or other obturator) or may be controlled (or not) by a control unit 21 for allowing gas venting should it be required.

The arterial expansion chamber 11 may also possibly include a further access 23 (service access) for receiving further fluids, medicaments or other substances in the chamber.

In relation to the set level of blood in the arterial expansion chamber 11, it should be noted that in general this level must be within a range of depths between a low value and a high value. Within these blood level values in the chamber it may be assumed that the equipment is working in a safe state: below, or above the low and high levels, and particularly during treatment, problems of various natures can arise, which will be more precisely described in the following.

Not least, it should also be noted that the arterial expansion chamber 11 has a constant containment volume, i.e. the chamber, in detail, is made of a rigid and substantially non-deformable material.

The extracorporeal circuit also comprises at least an expansion chamber 12 which operates on the venous blood return line 7, downstream of the first chamber 3 and upstream of the vascular access that returns the blood to the patient P.

At least a pressure sensor 14 is configured to detect at least a parameter relating to the pressure of the fluid present in the venous expansion chamber 12.

In general, the sensor 14 is configured such as to emit a signal corresponding to a measured value of the parameter, e.g. the pressure, and to forward it to a control unit 21 on each measurement carried out in successive moments of time Note that the detection of the pressure parameter may also be carried out in close proximity of the venous expansion chamber 12, for example by means of a transducer located in the section of pipe between the expansion chamber 12 and the venous return vascular access to the patient P or in the section of pipe between the first chamber 3 and the venous expansion chamber 12.

In any case a possible proper positioning of the pressure sensor 14 is such that it is directly active in the venous expansion chamber 12 at an upper portion thereof where normally (in use) a gas is housed.

It should further be noted that the venous expansion chamber 12 is generally intended in use to house a predetermined quantity of gas in an upper portion and a predetermined amount of blood at a predetermined level in a lower portion thereof.

The expansion chamber 12 has an inlet 12a for the blood in fluid connection with a first part of the return line 7 connected to the first chamber 3.

Through the inlet 12a, the chamber 12 receives treated blood from the filtration unit 2 in inlet to the chamber itself. In general, the inlet may be positioned at a base portion of the expansion chamber arranged, in use, to be directed downwards and in particular always occupied by blood.

In an embodiment the inlet may be in connection with a channel internal of the venous expansion chamber 12 which exhibits an outlet in the chamber itself at a predetermined height in relation to the base.

The venous expansion chamber further comprises an outlet 12b for the blood in fluid connection with the extracorporeal circuit 8 in order, in use, to cause blood exiting from the chamber to flow towards the vascular access to the patient P. The outlet 12b is also positioned at a base portion of the expansion chamber 12 arranged, in use, to be directed downwards and in particular always occupied by blood. The venous chamber 12 also internally houses a venous filter 35 which separates the outlet 12b from the remaining volume of the chamber 12.

The venous filter 35 helps avoiding air bubbles reaching the patient since bigger bubbles are broken and the generated small air bubbles trapped in the venous chamber.

The expansion chamber 12 also exhibits a ventilation opening 16 configured such as to allow, in use, gas passage to or from the expansion chamber 12, for example to or from the external environment.

The apparatus further comprises at least an actuator 18 operating on the ventilation opening 16 (for example on a channel connected thereto) for selectively inhibiting or allowing the passage of gas. The ventilation opening 16 is in particular arranged at an upper portion of the expansion chamber 12 arranged, in use, to be facing upwards, and even more in particular intended to be always occupied by the gas.

The actuator 18 may be an air pump or even a simple clamp (or other obturator) controlled or not by a control unit 21 for allowing gas to vent should it be necessary.

The venous expansion chamber 12 may also possibly include a further access 24 (service access) for receiving fluids or medicines or more in the same chamber.

Also, with reference to the set level of blood in the venous expansion chamber 12, it should be noted that in general the level must be within a range of predefined heights between a low value and a high value (possibly and in general different from the maximum and minimum levels of the arterial expansion chamber). If the blood level in the chamber is within these parameters, it may be assumed that the equipment is working in a safe state; if the level is below or above the minimum and maximum levels, problems of various nature may arise, which will be more specifically described in the following.

Not least, it should also be pointed out that the venous expansion chamber 12 also has a constant containing volume, i.e. the chamber is made of a rigid and substantially non-deformable material.

The apparatus 1 further comprises a first fluid flow intercept organ 20 operating on the removal line 6 upstream of the blood pump 9 and the arterial expansion chamber 11 and at least a second fluid flow intercept organ 22 operating in the return line 7 of the blood to the patient downstream of the venous expansion chamber 12. The intercept organs 20, 22, for example each constituted by a respective clamp controlled by the control unit 21, are arranged in the vicinity of the ends 33, 34 of the respective lines connectable to the patient P.

The apparatus may also include an air-bubble sensor 19 connected to the control unit 21 and capable of generating a signal that, if above a predetermined threshold, determines the generation of a closing command of the intercept organ 22 and shuts down the blood pump 9. In particular the device 19 is located on the blood return line 7, and still more in particular downstream of the venous expansion chamber 12 along the blood flow direction in the extracorporeal circuit. The air-bubble sensor 19 is known in the art and may use ultrasound to detect air bubbles in the blood.

In practice, the blood removal line 6, the arterial expansion chamber 11, the first chamber 3 of the treatment unit, the return line 7 of the blood to the patient and the venous expansion chamber 12 are part of an extracorporeal blood circuit 8, which, during use of the apparatus 1, provides for the circulation of blood externally of the body of the patient undergoing treatment.

The apparatus 1 further comprises at least a fluid evacuation line 10 connected with an outlet port of the second chamber 4 such as to receive at least a filtered fluid through the semipermeable membrane 5.

The evacuation line receives the waste fluid coming from the second chamber of the unit 2, for example, comprising used dialysis liquid and/or ultrafiltered liquid through the membrane 5.

The evacuation line 10 leads to a receiving element 27, for example consisting of a collection bag or a drainage pipe for the waste fluid. One or more dialysate pumps 28 may operate on the evacuation line 10: for example in the accompanying drawings a pump 28 active on the line 10 is provided. Note that the structure of the evacuation line 10 may also be different to the one illustrated (as long as it can properly drain the fluid exiting from the second chamber 4): for example the evacuation line 10 may comprise a single line as shown in the accompanying figures or a main drainage line and an ultrafiltration line branching from the main discharge line and provided with a respective pump (solution not illustrated).

In the example of FIG. 1, a dialysis line 25 is also present, for supplying a fresh treatment fluid in inlet to the second chamber 4: the presence of this line is not strictly necessary since, in the absence of the line 25, the apparatus is still able to perform treatments such as ultrafiltration, hemofiltration or plasmafiltration. In the case in which the dialysis line 25 is present, a fluid intercept organ 26 may be used to selectively allow or inhibit fluid passage through the dialysis line 25, depending on whether or not a purification by diffusive effect is to be performed inside the treatment unit.

The dialysis line 25, if present, is typically equipped with dialysis pump 29 and is able to receive a fresh fluid from a module 30, for example a bag or a section of on-line preparation of dialysis fluid, and to send such a fluid in inlet into the second chamber 4. Finally, the apparatus 1 may comprise one or more infusion lines of a replacement fluid: for example an infusion line 31 may be provided connected to the removal line 6 an or an infusion line 32 connected to the blood return line 7. The pre- and/or post-infusion lines 31, 32 may be supplied by suitable bags or directly by the fresh dialysis fluid prepared on-line.

These lines are only schematically represented in the accompanying figures, and are not further described as they are not relevant for the purposes of the description of the present invention.

The apparatus is also provided with at least a control unit 21. The control unit 21 may comprise one or more digital modules, for example of the microprocessor type, or one or more analog modules, or a suitable combination of digital and analog. As illustrated in the example of FIG. 1, the control unit 21 is connected with the blood pump 9 and/or with the dialysate pump 28 and/or with the dialysis pump 29, as well as with the pressure sensors 13, 14 of the arterial and venous expansion chambers 11, 12 and optionally, if present, with auxiliary pressure sensors. In addition the control unit may be connected to the fluid intercept organs 20, 22 and, if present, 25.

The control unit 21 is also in communication with the bubble detection device 19, with the module 30 (if the preparation is on-line) and possibly with the actuators 17, 18 on the ventilation lines 15 and 16.

The control unit 21 is configured or programmed to perform the procedures described below. If the control unit is of the programmable type, this unit is connected with a data carrier for storing instructions that, when performed by the control unit, carry out the procedures described below and illustrated by way of example in FIGS. 2, 3 and 4. The data carrier may comprise a mass storage, for example, optical or magnetic, a re-programmable memory (EPROM, FLASH) or a memory of another type.

In general (see also the flow diagram of FIG. 2), before start of treatment, the apparatus 1 is subjected to a priming procedure controlled by the control unit 21.

In particular, prior to treatment, a saline solution is fed into the extracorporeal circuit to wash and remove any air and residual particles.

At the end of this procedure, a predetermined level of saline at the desired pressure is established in the arterial and venous expansion chambers 11, 12.

Once the patient is connected to the equipment via the vascular access, the control unit 21 is configured to move at least the blood pump 9 at the beginning of a treatment to create, in the expansion chambers 11, 12, a corresponding set blood level in the lower portion, while confining a complementary quantity of gas in the upper portion.

The processing at this point continues for the duration $T_{tot}$ required in order to appropriately treat the blood taken from the patient P.

Throughout the treatment the blood level in the arterial and venous expansion chambers 11, 12 continuously changes (although by small amounts) at least as a result of the fact that the control unit 21 moves the blood pump 9 to generate a variable flow of blood Q(t) comprising a constant flow component $Q_b$ equal to a desired blood flow value and a variable flow component Qvar(t) at substantially zero average value. This is due in particular to the fact that the blood pump is peristaltic in nature and therefore produces a non-constant flow of blood in the circuit, as it is related to the successive crushing actions of the pump section 6a by the roller/rollers associated to the pump rotor.

In other words, the head of the treated fluid is given by a constriction which runs along the tube. In the example described, the pump 9 is constituted by a rotor to which two (or more rollers) are applied, which rotate to "choke" the tube and cause the advancement of the fluid.

Alternatively linear peristaltic pumps may be used (for example, "finger" pumps) or also other actuators capable of generating a pulsating movement in the blood, i.e. a non-constant flow, but oscillating about an average flow value.

Consequently the variable blood flow generates in the expansion chamber (both arterial 11 and venous 12) a pressure trend that is time-variable P(t) comprising a pressure component $P_{var}(t)$ oscillating about an average value $P_{avg}$.

Figure 5:
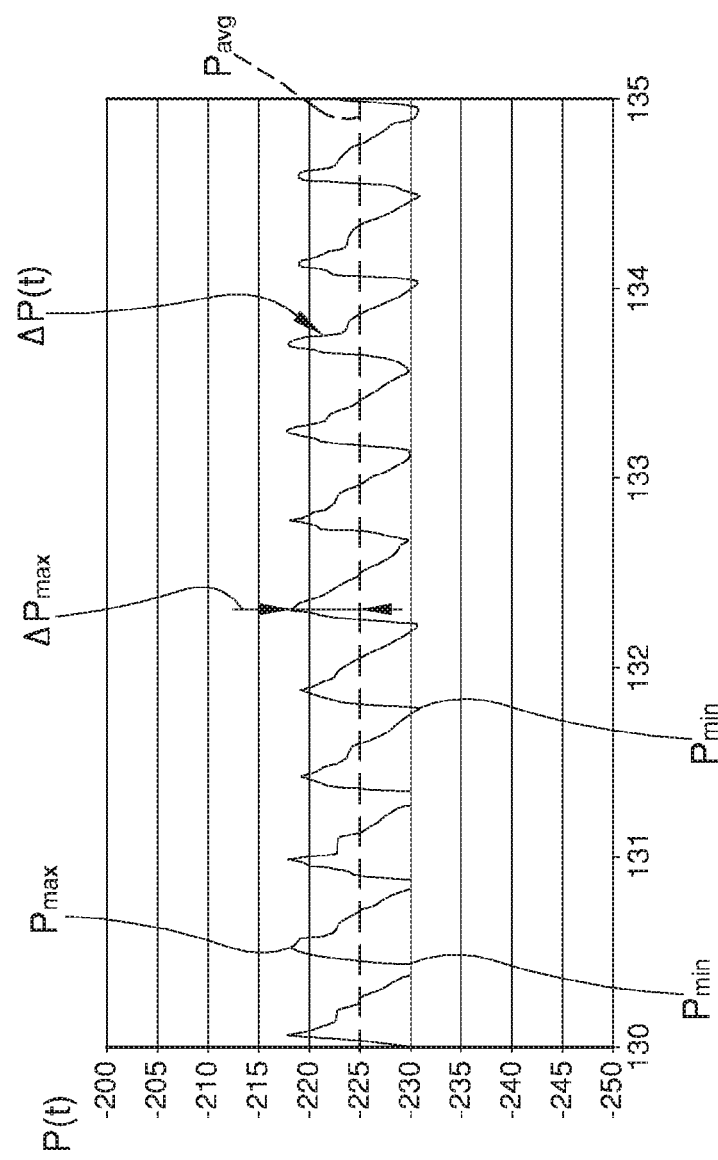
FIG. 5 shows the pressure progression over time in the arterial chamber.

An example of the pressure trend in an arterial chamber is shown in FIG. 5 where, the measurements performed by the pressure sensor 13 over a short time interval are represented.

This graph shows the average pressure Pang and the oscillatory behaviour (non-symmetrical, but at a substantially zero mean value) of the pressure $P_{var}(t)$ can clearly be observed, i.e. the oscillating component of the pressure.

The control unit 21 receives a plurality of measured pressure values $P_j$ from the pressure sensors 13, 14 located in the respective chambers for a predetermined period of time T. In general, pressure detection is performed throughout at least the entire period $T_{tot}$ coinciding with the treatment period.

Obviously the pressure values $P_j$ are measured in discrete and successive time instants $t_j$. The sampling timing may be constant, depending on the type of pressure sensor used and possibly other parameters of apparatus operation.

The underlying principle implemented by the control unit 21, and described below in detail, is to use the pressure component $P_j$ measured at various instants $t_j$ in order to assess the level of blood in the expansion chamber; also verification may be made of the permanence at a set level or in any case a safety level that substantially ensures the absence of air invasion into the removal and/or return lines 6, 7.

First, the control unit 21 calculates, as a function of the pressure values $P_j$ received by the respective sensor 13, 14, the average value $P_{avg}$ of the pressure P(t) at least in the chamber the control procedure described below is to be carried out (and in general this is done for both expansion chambers 11, 12).

Again in general terms, an estimated volume change value ΔV is also acquired in the expansion chamber 11; 12 linked to the variable flow component $Q_{var}(t)$ as better clarified in the following.

Then a calculation is made, as a function of the measured values of pressure $P_j$, of an estimated pressure variation value ΔP in expansion chamber 11;12 representative of the oscillating pressure component $P_{var}(t)$.

Finally the control unit 21 determines a value representative of a blood level L in the expansion chamber 11; 12 as a function of the mean value $P_{avg}$ of the pressure P(t), the estimated volume change ΔV and the estimated pressure variation value ΔP in the expansion chamber 11; 12.

The general operations mentioned above are carried out iteratively at predetermined moments during the treatment, for example in the blood processing condition when all of the transients (in particular start of treatment or after an interruption) have taken place.

In other words, the process of calculating the representative value of the blood level L in the expansion chamber 11; 12 is performed a plurality of times (n times) during apparatus operation to ensure a constant monitoring of the level; only those stages of the transition in which the measure could be distorted/affected due to non-stationary operating or non-operational states are excluded.

Given the above, the minimum period of time T for which the pressure data detected $P_j$ are used for calculations of the above-mentioned magnitude (which in general, though not necessarily, will be the volume occupied by air $V_{air}$ in the expansion chamber) comprises at least one, and in particular a plurality, of pressure oscillations around the mean value $P_{avg}$.

It is clear that a good time T is such as to allow a measurement as accurate as possible of the average pressure and the other indicated parameters and therefore, the longer the time T, the better the estimate.

However there is also a need for estimation frequency and updating of the data relating to the level, so that for the purposes of the implementation of the present invention, periods of time were used for each calculation of the representative value of the blood level L (this procedure will be described in detail in the following) dependent on the set blood flow and variable from 8 to 13 pressure oscillations around the mean value $P_{avg}$ (i.e. from 4 to 6.5 rotations of the peristaltic pump 9).

Again from the general point of view, the control unit 21 is programmed to determine the magnitude representative of the blood level in the expansion chamber 11; 12 (which will be for example the air volume $V_{air}$ in the expansion chamber), exploiting the ideal gas law.

By operating in this way a measurement may be obtained of the magnitude (for example the volume of air) exclusively by means of pressure measurements, i.e. the use of additional sensors such as flow sensors or additional pressure sensors is not necessary.

In this regard the ideal gas law is applied to a modelled representation of the apparatus substantially constituted by a superposition of an open system in which the expansion chamber 11; 12 is considered to be in the steady state and affected solely by the constant flow $Q_b$ component, and the pressure inside the expansion chamber is correspondingly a constant pressure that is equal to the average value $P_{avg}$, and a partially-closed system in which only an inlet to the expansion chamber 11; 12, selected from the inlet 11a; 12a for the blood and the outlet 11b; 12b for the blood, is open and subject to; a volume change ΔV representative of the variable flow component $Q_{var}(t)$ oscillating around the constant component $Q_b$; and to a corresponding change in pressure ΔP representative of the pressure component oscillating $P_{var}(t)$.

A measure of the volume of air $V_{air}$ is then obtained from the pressure information received, and by applying the ideal gas law to the system described above.

In detail, the volume of air $V_{air}$ in the expansion chamber is given by the following relation:

$$Vair = \Delta V \cdot \frac{(P_{avg} + \Delta P)}{(\Delta P)}$$

in which:

$V_{air'}$ is the volume of air inside the expansion chamber (11; 12);

'ΔV' is the volume variation linked to the variable flow component (Qvar(t));

'$P_{avg}$' is the average pressure value (P(t));

'ΔP' is the pressure variation in the expansion chamber (11, 12) representing the oscillating pressure component ($P_{var}(t)$).

The accuracy of the measurement obviously depends on the accuracy of the estimation of ΔV, ΔP and also $P_{avg}$ will be affected by the approximations linked to the model used which is applied to a non-linear system; however this last error will be substantially negligible as ΔP is sufficiently small with the aim of not significantly influencing the flow $Q_b$.

Further, as shown in the following, the non-linearities may optionally be compensated with a consequent increase in the accuracy of measurement.

Figure 4:
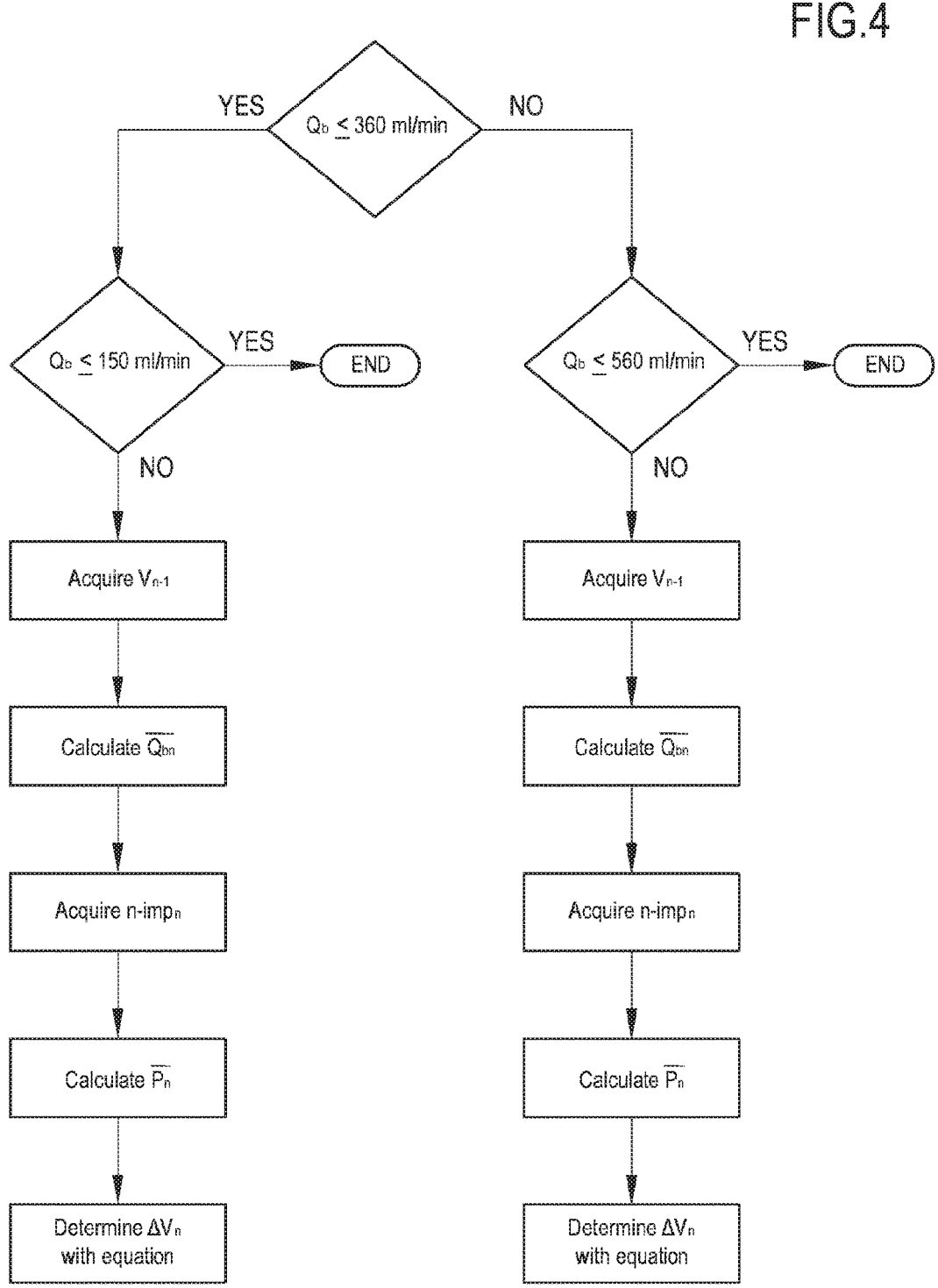
FIG. 4 shows a flow diagram illustrating the calculation of the estimated value of volume change.

In relation to the step of acquiring the estimated volume change value ΔV in the expansion chamber 11; 12, there exist different operating modes (two are illustrated in the block diagram of FIG. 4).

In a first example the acquisition includes a substep of reading, from a memory, an estimated pre-set volume change value ΔV, for example an estimated value entered by an operator or pre-stored in the machine.

In fact, the volume change ΔV may be determined a priori by a study of the geometry of the pump section 6a and the geometry of the peristaltic pump 9.

In fact, this volume change ΔV exactly corresponds to the fluid which is periodically moved due to the crushing of the pipe section on which each roller of the pump 9 acts.

Therefore, once the geometry of these components and their coupling is known an estimation may be made of a 'nominal' volume change ΔV and set for the calculation as a constant value.

In a more refined alternative, the estimated volume change value ΔV is selected by the control unit 21 from among a plurality of possible pre-set estimated values and the choice is made in particular as a function of at least one or more of the following parameters: a type of extracorporeal circuit installed on the equipment, a type of extracorporeal treatment apparatus, a type of blood pump 9, the desired or set value of blood flow $Q_b$, a pressure upstream or downstream of the blood pump 9, a type of pump section 6a, the average pressure $P_{avg}$ detected in expansion chamber 11, 12, an index of ageing of the pump section 6a, the number of revolutions accumulated by the blood pump 9, etc. . . . .

In other words, a plurality of constant volume change values ΔV may be stored, but different from each other, and the one that best approximates to the real situation may be used.

It has been observed that the volume change ΔV is influenced by predetermined operating parameters of the machine, among which the ageing of the tube, but also the set blood flow $Q_b$ or the pressure existing at the time of the thrust.

Therefore, the control unit 21, having these parameters available may, from time to time, select the volume change value ΔV most appropriate and responding to reality.

In a further alternative the volume change value may be calculated for each measurement.

In the latter case (diagram of FIG. 4) the step of acquiring an estimated volume change value ΔV in expansion chamber 11; 12 comprises a sub-step of calculating the estimated value as a function of at least one (or more) of the following parameters: the values of pressure $P_j$ measured, the value of the constant component of blood flow $Q_b$, an indicator of aging of a pump tract 6a (for example the indicator is the number of revolutions accumulated by the pump 9 at the time of estimation of volume change ΔV in the expansion chamber 11; 12, or in the number of pulses of an encoder that detects a passage of the rollers of the peristaltic blood pump 9) and a previously-estimated air volume change value of Vn−1 in the expansion chamber 11, 12.

By way of example, in the present embodiment, it was decided to use two different mathematical relationships as a function of the set blood flow $Q_b$ as it was found that in the presence of lesser flows only predetermined variables play an effect on the ΔV estimate, while at higher values other not-negligible variables come into play.

The mathematical relationship adopted in the case in which the average value of the blood flow $Q_b$ is less than 400 ml/min and up to 100 ml/min (in detail when $150 \leq Q_b \leq 360$ ml/min) is:

$$\Delta V_n = k_0 + k_1 \cdot \overline{P_n} + k_2 \cdot n_{imp_n} + k_3 \cdot \overline{Q_{b_n}} + k_4 \cdot V_{n-1}$$

in which:

n is the generic index indicating the nth measurement output of the air volume $V_{air}$;

ΔVn is the estimated variation of volume ΔV at the n-th step of measurement of the air volume $V_{air}$;

$k_0, k_1, k_2, k_3, k_4$ are experimentally-determined constants;

$\overline{P_n}$ is the average of the pressure values measured at the end of the n-th measuring step of the air volume $V_{air}$;

$n\_imp_n$ is the accumulated number—o a value proportional to the accumulated number—of revolutions of the blood pump (9);

ΔVn is the average value of the blood flow at the end of the n-th measuring step of the air volume $V_{air}$;

$V_{n-1}$ is the estimated measurement of the air volume obtained from the preceding calculation.

In other terms the estimate of the n-th variation in ΔV (i.e. the n-th calculation of this value) is considered to be connected to a series of constant values that are experimentally determined, for example by acquiring functioning data of machines and estimating with precision a value then used in the subsequent calculations; these values are the index of the importance in the calculation of the volume variation of other functioning parameters of the apparatus (for example the blood flow $Q_b$ or the pressure $P_j$).

Further, it has been observed that this value is also affected by the average of the pressure values measured at the end of the n-th measurement step of the air volume $V_{air}$ (i.e.

$$\frac{\Sigma_{j=1}^{N} P_j}{N}),$$

as well as the set blood flow $Q_b$ and by the previously-estimated value of the air level $V_{air}$ at measurement n−1 (or in any case in a previously-performed estimate with respect to the present one).

In this example importance has also been given to the influence of the aging of the pump section 6a which, over time and following successive crushing, loses elasticity and this influences the volume of blood moved by the rollers of the blood pump 9.

For average values of the blood flow $Q_b$ greater than 300 ml/min and lower than 650 ml/min (in detail when $360 \leq Q_b \leq 580$ ml/min), a better approximation of the volume variation $\Delta V$ has been observed, exploiting a slightly different relation:

$$\Delta V_n = k_0 + k_1 \cdot \overline{P_n} + k_2 \cdot n_{imp_n} + k_3 \cdot \overline{Q_{b_n}} + k_4 \cdot V_{n-1} + k_5 \cdot \overline{P_n}^2$$

in which:

n is the generic index indicating the n-th measurement output of the air volume $V_{air}$;

$\Delta V_n$, is the estimated variation of volume $\Delta V$ at the nth step of measurement of the air volume $V_{air}$;

$k_0, k_1, k_2, k_3, k_4, k_5$ are experimentally-determined constants;

$\overline{P_n}$ is the average of the pressure values measured at the end of the nth measuring step of the air volume $V_{air}$;

$n\_imp_n$ is the accumulated number—or a value proportional to the accumulated number—of revolutions of the blood pump 9;

$\Delta V_n$ is the average value of the blood flow at the end of the nth measuring step of the air volume $V_{air}$;

$V_{n-1}$ is the estimated measurement of the air volume obtained from the preceding calculation.

Note that, with respect to the preceding relations, an additional parameter has been introduced related to the square of the average of the pressure values taken into account.

Moreover, the meaning of all terms introduced appears the same in both equations.

Note that only the values of the constants k may be different between the first and the second equation presented above.

Figure 3:
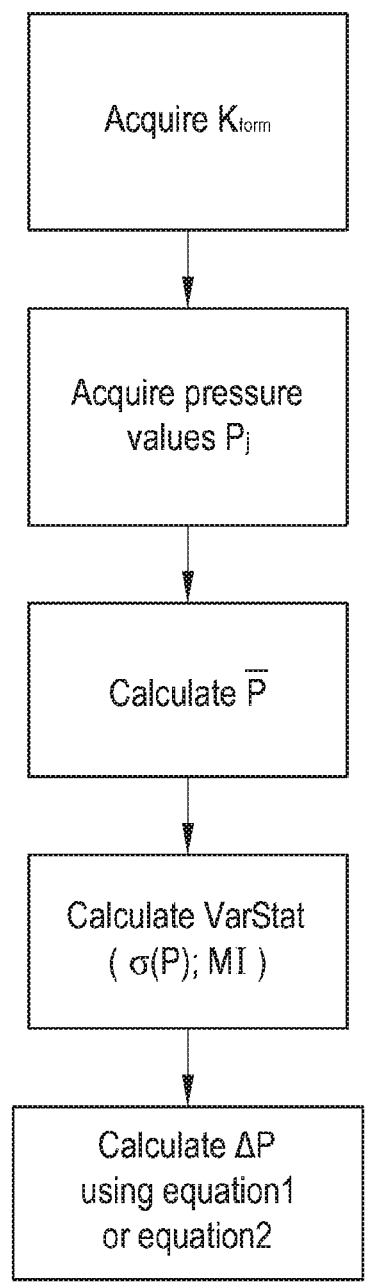
FIG. 3 is a flow diagram illustrating the calculation of the estimated value of variation of oscillating pressure.

Also the pressure variation value $\Delta P$ consequent to the above-cited volume change $\Delta V$ must be properly estimated (diagram of FIG. 3).

On varying the blood level in the expansion chamber in fact the maximum and minimum values of $\Delta P$ in the various filling conditions of the chamber vary, in particular the maximum amplitude of $\Delta P_{max}$ of oscillation pressure $\Delta P$ (i.e. the difference between maximum peak $P_{max}$—or minimum peak $P_{min}$—and the average value of pressure $P_{avg}$ of each oscillation) decreasing from the situation of the standard level to that of the minimum—or unsafe—level.

In these terms, the pressure variation value $\Delta P$ that could be adopted could be, for example, the maximum amplitude between $\Delta P_{max}$ maximum peak $P_{max}$ (or minimum peak $P_{min}$) and the average pressure of each oscillation (or a value proportional thereto) or, alternatively, a statistical variable of that value such as an average of the maximum amplitudes $\Delta P_{max}$ of a predetermined number of contiguous oscillations (not necessarily, but in particular, consecutive) of pressure.

The applicant has however observed that this type of control value of the absolute nature (i.e. a value linked to the absolute measurements of maximum and minimum pressure subtracted from one another to eliminate the average pressure component), while providing a clear indication of direct pressure variation, and could therefore be clearly used as an estimate of $\Delta P$, is susceptible to improvement in one auxiliary aspect (non-essential) of the invention.

In fact the measurement of peak pressure values $P_{max}$ and $P_{min}$, gives rise to problems of calculation that are surmountable but relevant. It is in fact clear that it becomes necessary, firstly, to determine what are the maximum and minimum points in oscillating pressure situations and with measured pressure values that are discrete (each time interval $t_j$); further, the measurement is obviously subject to noise and detection errors which may be complex to take into account.

In this situation the use of an estimated value of the oscillating pressure $\Delta P$ which is a statistical indicator appears to greatly simplify the analysis.

In this regard, the step of calculating the estimated pressure variation value of $\Delta P$ is performed by the control unit 21 using a mathematical relationship that is a function of a statistical indicator VarStat representing of the oscillating pressure component $\Delta P$:

$$\Delta P = f\{\text{VarStat}\}$$

Particularly advantageous is the adoption of a statistical indicator that is an index of dispersion concisely describing a quantitative statistical distribution of the measured pressure values $P_j$; in particular the control value is a measure indicating the distance of the pressure $P_j$ values from a central value, for example, identified with the average pressure value $P_{avg}$ or the pressure median.

By operating in this manner it becomes irrelevant to determine which are the maxima and minima of the pressure detected in the window of time established for the analysis, as substantially each measured value $P_j$ contributes to determining the component of the oscillating pressure $\Delta P$ (obviously it might be decided to discard certain measured pressure values, for example, as clearly erroneous—greater than or less than $P_{max}$-admissible or less than $P_{min\text{-}admissible}$—or not to consider all the values measured on the basis of other calculation optimization logics).

In the case now described the statistical indicator VarStat, which is used to estimate of the pressure change $\Delta P$ is the standard deviation $\sigma(P)$ or, alternatively, is the average integral MI, in particular the demodulated average integral.

Alternatively, other indicators may be used, such as statistical variance, field or interval of variation, the average absolute difference, standard deviation, coefficient of variation, Median absolute deviation, interquartile range, Poisson dispersion index.

The statistical indicator VarStat of measured pressure values $P_j$ is typically calculated on a plurality N of measured pressure values $P_j$, in particular N is greater than 6 and even more particularly N is at least 10.

In greater detail the step of calculating the estimated pressure variation value $\Delta P$ is performed by means of a mathematical relationship that is a function of the statistical indicator VarStat representing of the oscillating pressure component $\Delta P$ and an experimentally-obtained constant $K_{form}$ according to the following relation:

$$\Delta P = K\text{form} \cdot \text{VarStat}$$

The statistical indicator VarStat representing the oscillating pressure component $\Delta P$ is defined as:

$$\sigma(P) = \sqrt{\sum_{t=1}^{N} \frac{(P_j - \overline{P})^2}{(N-1)}}$$

in which:

N is the number of pressure measurements carried out in the reference time interval $T_n$ comprising a plurality of pressure oscillations $P_j$;

$P_j$ is the generic j-th pressure measurement;

$\bar{P}$ is the average pressure calculated in the reference time interval $T_n$.

An alternative hypothesis of the calculation of the oscillating pressure component $\Delta P$ comprises filtering some disturbances, in particular frequency disturbances such as those induced by a heart-beat.

Figure 6:
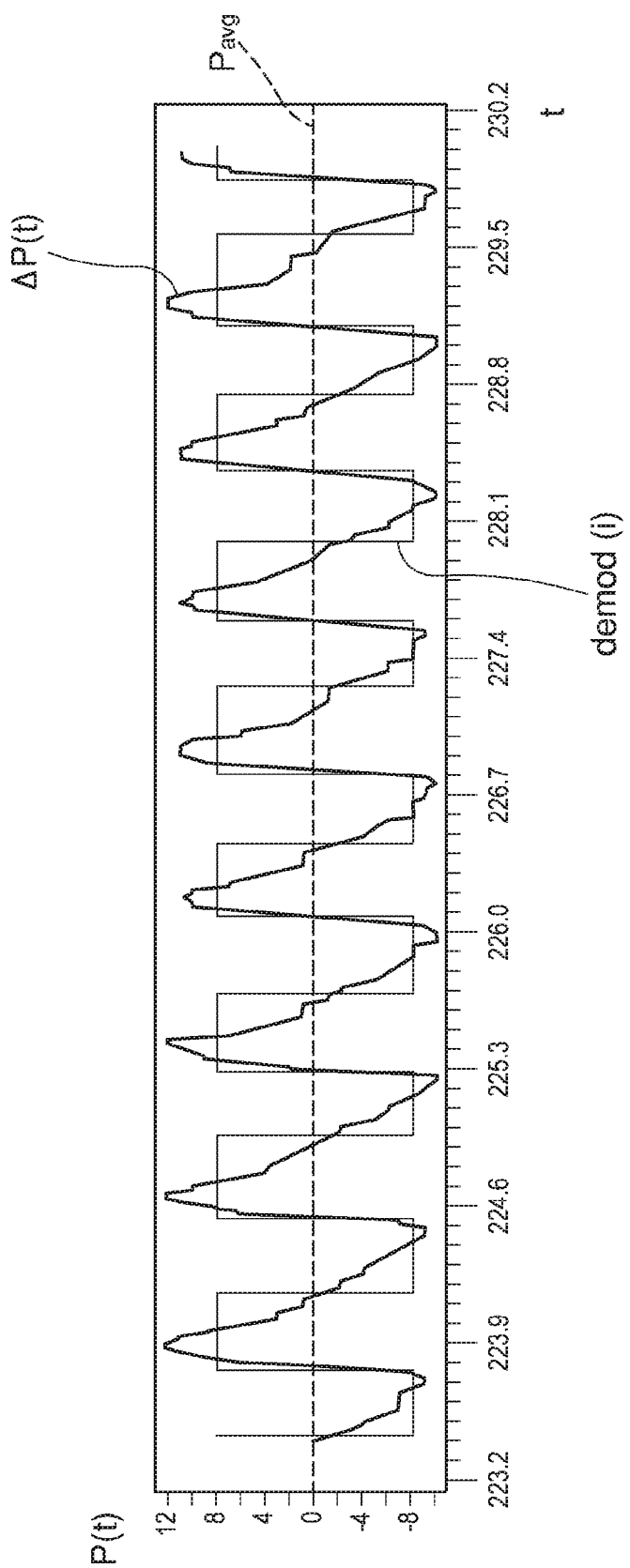
FIG. 6 shows the progression of the pressure over time in the arterial chamber in superposition to a synchronous demodulating square wave.
Figure 7:
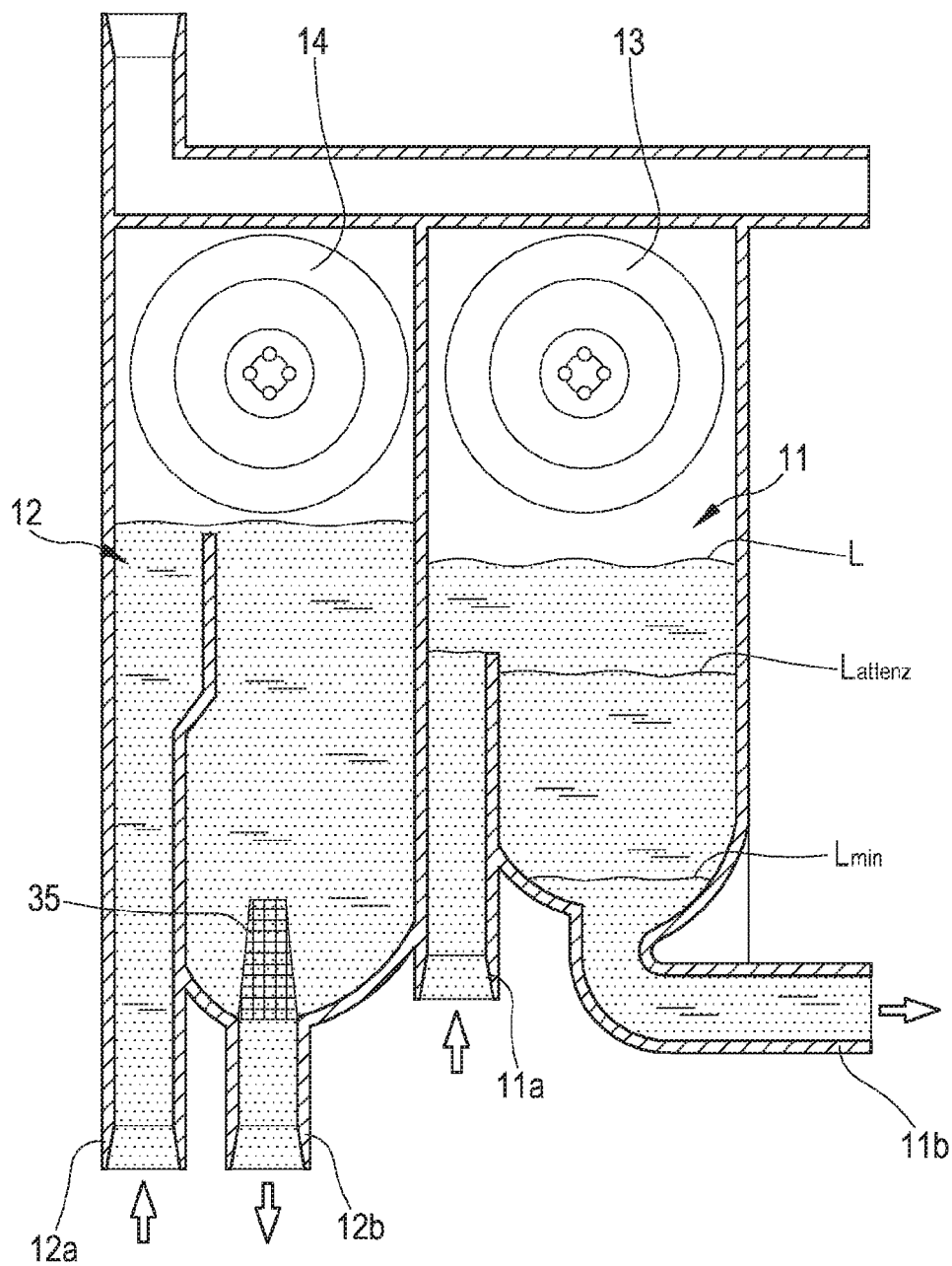
FIG. 7 is a detailed illustration of the arterial and venous expansion chambers and also illustrates the values of the alert level and minimum threshold.

This approach exploits a relation of the type:

$$\Delta P = K_{form} \cdot \text{VarStat}$$

with the constant $K_{form}$ obtained experimentally (not necessarily coinciding in value with the previously-described one) and in which the statistical indicator VarStat representing the oscillating pressure component $\Delta P$ is defined as:

$$\sigma(P) = \frac{1}{N} \cdot \sum_{i=1}^{N} (P_j - \bar{P}) \cdot demod(i)$$

in which:

N is the number of pressure measurements carried out in the reference time interval $T_n$ comprising a plurality of pressure oscillations $P_j$;

$P_j$ is the generic j-th pressure measurement;

$\bar{P}$ is the average pressure calculated in the reference time interval $T_n$, demod(i) is a square wave of single amplitude synchronised with the blood pump 9 and in phase with the peristaltic pulse (see FIG. 6).

By operating as described above, the control unit is able to determine a magnitude, i.e. the volume of air $V_{air}$, directly connected to the level of blood in the expansion chamber 11; 12. Where the control unit 21 determines that in any of the expansion chambers 11, 12, the apparatus is in a blood level condition L considered an alert condition ($L_{attenz}$), an alarm situation is generated in which at least an audible and/or visual alarm is used to call an operator who may verify the actual blood level and possibly correct the potentially dangerous situation.

It is also possible that the control unit 21, in the event of verification of a level of blood in the arterial and/or venous expansion chamber 11, 12, below a minimum level $L_{min}$ (possibly different from the level of attention $L_{attenz}$ in which operator intervention is required) commands actuators active at least on the extracorporeal blood circuit 8 and thus places the patient in a safe condition.

For example, the control unit 21 may command at least the blood pump 9 to reduce or zero the flow of blood in the extracorporeal blood circuit 8 and substantially cancel the passage of fluid through the semipermeable membrane 5 of the treatment unit 2 (if present).

In more advanced equipment the control unit 21 may be programmed so that, in the event of verification of a level of blood in the expansion chamber 11, 12 (possibly only in an alert situation), it commands the respective actuator 17, 18 relative to the chamber in which the problem has occurred to allow the passage of gas through the ventilation opening 15, 16 re-establishing the correct level of blood in the chamber.

In particular, since in general identified a situation of low blood level is identified, the control unit commands the actuator 17, 18 to allow the passage of gas exiting from the ventilation opening 15, 16.

Finally, the control unit 21 may also perform a check of the consistency of the data collected and calculated. In particular, the control unit 21 may be programmed to compare the value of the calculated blood level (L) with at least one of a maximum permissible threshold ($L_{max}$) and a minimum permissible threshold ($L_{min}$) in order to determine if the level of blood is within a correct operating range of ($L \leq L_{max}$; $L \geq L_{min}$) and to signal a malfunctioning of the calculating system if the level of blood is outside the proper operating range.

In addition (or alternatively) the consistency check may also be carried out on individual measured pressure values $P_j$ checking whether a plurality thereof is outside a reasonable range of functionality.

In fact, the pressure sensor of the expansion chamber is substantially the only component of the apparatus (in addition to the control unit) to be needed in order to perform the verification function; and the analyses mentioned above have the main purpose of verifying failure or anomaly relevant enough to affect detection.

It is clear that the control unit 21 is programmed to perform the above-mentioned steps in relation to the arterial expansion chamber 11 located on the blood removal line 6 and/or in relation to the venous expansion chamber 12 located on the blood return line 7.

In particular, the adoption of this analysis in relation to the arterial chamber appears very advantageous because in general the expansion chambers upstream of the treatment unit 2 are not provided with level sensors and/or other pre-unit security systems 2 and therefore air that might enter the removal line 6 is arranged to reach the treatment unit and be transformed into a plurality of micro-bubbles by the treatment unit, therefore becoming more difficult to detect downstream in the return line 7.

Obviously, the described methodology may be used in each expansion chamber that may be present on the extracorporeal circuit (in addition to or in replacement of the expansion chambers described).

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. A method for reducing the risk of infusion of gas microbubbles in a patient, the method comprising:

moving a first actuator to generate a variable flow comprising a constant flow component of a desired flow value and a variable flow component oscillating about the constant flow component, the variable flow component generating in an expansion chamber a pressure progression that is variable in time, the pressure progression comprising a pressure component oscillating about a mean value;

receiving from at least one sensor associated with the expansion chamber and configured to sense pressure values internally of the expansion chamber, a plurality of pressure values for a time period comprising a plurality of pressure oscillations about the mean value, the pressure values being measured at successive time instants;

calculating, as a function of the pressure values, an average pressure value;

acquiring an estimated volume variation value in the expansion chamber linked to the variable flow component;

calculating, as a function of the pressure values in the expansion chamber, an estimated pressure variation value that is representative of the oscillating pressure component; and determining a magnitude that is representative of a level in the expansion chamber as a function of the average pressure value, the estimated volume variation value and the estimated pressure variation value.

2. The method of claim 1, further including determining the representative magnitude of the level in the expansion chamber by exploiting the ideal gas law, wherein the ideal gas law is applied to a modelled representation of an apparatus substantially constituted by a superposing of:

an open system in which the expansion chamber is considered to be in a stationary state and affected solely by the constant flow component and the internal pressure in the expansion chamber is correspondingly a constant pressure equal to the mean value; and a partially closed system in which only an access to the expansion chamber, selected from between an inlet and an outlet, is open and subject to a volume variation representative of the variable flow component oscillating about the constant flow component and a pressure value representing the oscillating pressure component.

3. The method of claim 2, further including determining an air volume in the expansion chamber.

4. The method of claim 1, further including determining the magnitude representing the level in the expansion chamber using the following mathematical relation:

$$Vair = \Delta V \cdot \frac{(Pavg + \Delta P)}{(\Delta P)}$$

wherein:

$V_{air}$ is a volume of air inside the expansion chamber;

$\Delta V$ is a volume variation linked to the variable flow component;

$P_{avg}$ is the average pressure value; and $\Delta P$ is the estimated pressure variation value in the expansion chamber representing the oscillating pressure component.

5. The method of claim 1, further including calculating the average pressure value as a function of a plurality of measured pressure values relating to a time period comprising a plurality of flow oscillations about the constant flow component and consequently a plurality of oscillations of the pressure about the average value, the time period comprising at least three oscillations.

6. The method of claim 5, wherein the time period is a function of the constant flow component.

7. The method of claim 1, wherein acquiring the estimated volume variation value in the expansion chamber comprises reading from a memory of an estimated pre-set value of volume variation, chosen between an estimated value entered by an operator and an estimated value selected by a control unit from among a plurality of possible pre-set estimated values.

8. The method of claim 1, wherein acquiring the estimated volume variation value in the expansion chamber comprises calculating the estimated value as a function of at least the measured pressure values.

9. The method of claim 1, wherein acquiring the estimated volume variation value in the expansion chamber comprises calculating the estimated value as a function of at least one of:

the constant flow component;

an indicator of an amount of use of a pump tract, the indicator being chosen among a number of revolutions of a pump accumulated at the moment of the estimation of volume variation in the expansion chamber and the number of pulses of an encoder which detects passage of rollers of the pump of a peristaltic type; or a preceding estimated value of a variation in air volume in the expansion chamber.

10. The method of claim 1, wherein acquiring the estimated volume variation value in the expansion chamber comprises calculating the estimated value using the following mathematical relation:

$$\Delta V_n = k_0 + k_1 \cdot \overline{P_n} + k_2 \cdot n_{imp_n} + k_3 \cdot \overline{Q_{b_n}} + k_4 \cdot V_{n-1}$$

wherein:

n is a generic index indicating the n-th measurement output of an air volume;

$\Delta V_n$ is an estimated variation of volume $\Delta V$ at the n-th step of measurement of the air volume;

$k_0, k_1, k_2, k_3, k_4$ are experimentally-determined constants;

$\overline{P_n}$ is an average of the pressure values measured at the end of the n-th measuring step of the air volume;

$n\_imp_n$ is an accumulated number or a value proportional to the accumulated number of revolutions of a pump;

$Q_{bn}$ is an average value of the flow at the end of the n-th measuring step of the air volume; and $V_{n-1}$ is an estimated measurement of the air volume obtained from a preceding calculation.

11. The method of claim 10, wherein the mathematical relation is adopted when the average value of the flow is less than 400 ml/min and greater than 100 ml/min.

12. The method of claim 1, wherein acquiring the estimated volume variation value in the expansion chamber comprises calculating the estimated value using the following mathematical relation:

$$\Delta V_n = k_0 + k_1 \cdot \overline{P_n} + k_2 \cdot n_{imp_n} + k_3 \cdot \overline{Q_{b_n}} + k_4 \cdot V_{n-1} + k_5 \cdot \overline{P_n}^2$$

wherein:

n is a generic index indicating the n-th measurement output of an air volume;

$\Delta V_n$ is an estimated variation of volume $\Delta V$ at the n-th step of measurement of the air volume;

$k_0, k_1, k_2, k_3, k_4, k_5$ are experimentally-determined constants;

$\underline{P_n}$ is an average of the pressure values measured at the end of the n-th measuring step of the air volume;

$n\_imp_n$ is an accumulated number or a value proportional to the accumulated number of revolutions of a pump;

$Q_{bn}$ is an average value of the flow at the end of the n-th measuring step of the air volume; and $V_{n-1}$ is an estimated measurement of air volume obtained with a preceding calculation.

13. The method of claim 12, wherein the mathematical relation is adopted when the average value of the flow is greater than 300 ml/min and less than 650 ml/min.

14. The method of claim 1, wherein calculating the estimated pressure variation value comprises using a mathematical relation which is a function of a statistical indicator representative of the oscillating pressure component:

$$\Delta P = f\{VarStat\}$$

wherein:

ΔP is pressure variation due to the oscillating pressure component; and

VarStat is a statistical indicator representative of the oscillating pressure component.

15. The method of claim 14, wherein the statistical indicator is a dispersion index summarily describing a quantitative statistical distribution of the measured pressure values, the statistical indicator being a measurement indicating a distance of the pressure values from a central value identified with the average pressure value.

16. The method of claim 14, wherein the statistical indicator is a standard deviation or an integral average.

17. The method of claim 14, wherein the statistical indicator of the measured pressure values is calculated on a plurality N of measured pressure values, N being greater than 6.

18. The method of claim 1, wherein calculating the estimated pressure variation value comprises using a mathematical relation that is a function of a statistical indicator which represents the oscillating pressure component and a constant obtained experimentally:

$$\Delta P = K_{form} \cdot \text{VarStat}$$

wherein:

$K_{form}$ is a constant obtained experimentally; and

ΔP is the oscillating pressure component.

19. The method of claim 14, wherein the statistical indicator representing the oscillating pressure component is defined as:

$$\sigma(P) = \sqrt{\sum_{i=1}^{N} \frac{(P_i - \overline{P})^2}{(N-1)}}$$

wherein:

N is a number of pressure measurements carried out in a reference time interval comprising a plurality of pressure oscillations;

$P_i$ is a generic i-th pressure measurement;

$\overline{P}$ is an average pressure calculated in the reference time interval; and σ(P) is the statistical indicator representing the oscillating pressure component.

20. Method according to claim 14, wherein the statistical indicator representing the oscillating pressure component is defined as:

$$\sigma(P) = \frac{1}{N} \cdot \sum_{i=1}^{N} (P_i - \overline{P}) \cdot demod(i)$$

wherein:

N is a number of pressure measurements carried out in a reference time interval comprising a plurality of pressure oscillations;

$P_i$ is a generic i-th pressure measurement;

$\overline{P}$ is an average pressure calculated in the reference time interval;

demod(i) is a square wave of single amplitude synchronised with the pump and in phase with the peristaltic pulse; and σ(P) is the statistical indicator representing the oscillating pressure component.

21. The method of claim 1, wherein the expansion chamber is provided with an apparatus for extracorporeal blood treatment, the apparatus comprising:

at least one treatment unit having at least a first chamber and at least a second chamber separated from one another by a semipermeable membrane;

at least one blood removal line connected to an inlet port of the first chamber and arranged to remove blood from a patient;

at least one blood return line connected to an outlet port of the first chamber and arranged to return treated blood to the patient;

the expansion chamber placed at least in one of the blood removal line or the blood return line, the expansion chamber configured to contain a predetermined quantity of gas in an upper portion and a predetermined quantity of blood at a predetermined level in a lower portion, the blood removal line, the blood return line, the first chamber and the expansion chamber being part of an extracorporeal blood circuit; and the first actuator being a blood pump operating in the extracorporeal blood circuit to move the blood in the circuit.

22. The method of claim 21, wherein the expansion chamber comprises at least one of an arterial expansion chamber located on the blood removal line, or a venous expansion chamber located on the blood return line, the blood pump being located downstream of the arterial expansion chamber along a blood transit direction.

23. The method of claim 22, which is carried out in relation to both to the arterial expansion chamber and to the venous expansion chamber.

24. The method of claim 21, wherein the pressure sensor is located in the expansion chamber, at a portion arranged to contain the gas.

25. The method of claim 21, wherein the expansion chamber includes an inlet for the blood in fluid connection with the extracorporeal circuit and an outlet for the blood in fluid connection with the extracorporeal circuit, the method including receiving blood in the inlet to the expansion chamber and causing blood to flow out of the outlet from the expansion chamber, the inlet and the outlet being positioned at a base portion of the expansion chamber arranged to face downwardly and be occupied by the blood.

26. The method of claim 21, wherein the expansion chamber includes a ventilation opening and the apparatus further comprises an actuator operating on the ventilation opening, the method including allowing a passage of gas from or towards the expansion chamber, the actuator selectively inhibiting or enabling the passage of gas, the ventilation opening being positioned at an upper portion of the expansion chamber arranged, in use, to face upwardly.

27. The method of claim 26, further including commanding the actuator to enable passage of gas to exit from the ventilation opening when a blood level in the expansion chamber is below a predetermined threshold.

28. The method of claim 21, further including commanding at least the blood pump to reduce or stop the blood flow in the extracorporeal blood circuit and at least substantially stop the passage of fluid through the semipermeable membrane of the treatment unit when a blood level in the expansion chamber is below a predetermined threshold.

29. The method of claim 21, further including activating the blood pump before the start of a treatment for creating in the expansion chamber the predetermined level of blood in the lower portion and confining a complementary quantity of gas in the upper portion.

30. The method of claim 11, which is carried out by a control unit of the apparatus for extracorporeal blood treatment.

31. The method of claim 1, further including comparing the determined level with at least one of a maximum admissible threshold and a minimum admissible threshold to determine whether the level is within a correct functioning interval, and signalling a malfunction if the level is beyond the correct functioning interval.

32. The method of claim 1, wherein the variable flow component has a substantially nil average value.

\* \* \* \* \*